(12) United States Patent
Nandi et al.

(10) Patent No.: US 11,020,349 B1
(45) Date of Patent: Jun. 1, 2021

(54) TRANSMUCOSAL DOSAGE FORMS OF REMDESIVIR

(71) Applicant: Jubilant Generics Limited, Noida (IN)

(72) Inventors: Indranil Nandi, Yardley, PA (US); Anil Jain, Noida (IN); Ganesh Vinayak Gat, Noida (IN)

(73) Assignee: Jubilant Generics Limited

( * ) Notice: Subject to any disclaimer, the term of this patent is extended or adjusted under 35 U.S.C. 154(b) by 0 days.

(21) Appl. No.: 16/929,005

(22) Filed: Jul. 14, 2020

(51) Int. Cl.
*A61K 9/20* (2006.01)
*A61K 9/00* (2006.01)
*A61K 31/675* (2006.01)

(52) U.S. Cl.
CPC .......... *A61K 9/2059* (2013.01); *A61K 9/2009* (2013.01); *A61K 9/2018* (2013.01); *A61K 9/2027* (2013.01); *A61K 9/2031* (2013.01); *A61K 9/2054* (2013.01); *A61K 9/2095* (2013.01); *A61K 31/675* (2013.01); *A61K 9/0053* (2013.01)

(58) Field of Classification Search
None
See application file for complete search history.

(56) References Cited

U.S. PATENT DOCUMENTS

2005/0112196 A1* 5/2005 Xie .......................... A61P 25/24
424/464
2017/0071964 A1* 3/2017 Clarke .................... A61P 31/12

OTHER PUBLICATIONS

Kinman, Sublingual and Buccal Medication Adminstration, Jun. 6, 2017. (Year: 2017).*

* cited by examiner

*Primary Examiner* — Melissa S Mercier
(74) *Attorney, Agent, or Firm* — William D. Hare, Esq.; McNeely, Hare & War, LLP

(57) ABSTRACT

Disclosed herein are the sublingual pharmaceutical compositions comprising remdesivir or its pharmaceutically acceptable salts or solvates thereof. The present invention also relates to a process for preparing sublingual pharmaceutical compositions comprising remdesivir or its pharmaceutically acceptable salts or solvates thereof. Compositions of remdesivir prepared as per present invention are able to increase bioavailability by avoiding first-pass metabolism. The compositions of remdesivir prepared as per present invention are useful in the treatment of viral infections including coronavirus infection (COVID-19). The compositions of remdesivir prepared as per present invention exhibit desired pharmaceutical technical attributes such as pH, assay, related substance, disintegration and dissolution.

20 Claims, No Drawings

TRANSMUCOSAL DOSAGE FORMS OF REMDESIVIR

FIELD OF THE INVENTION

The present invention relates to sublingual pharmaceutical compositions of remdesivir or its pharmaceutically acceptable salts or solvates thereof. In particular, but without restriction to the particular embodiments hereinafter described in accordance with the best mode of practice, the present invention provides sublingual pharmaceutical compositions comprising remdesivir or its pharmaceutically acceptable salts or solvates thereof and processes for preparing these compositions to increase bioavailability by avoiding first-pass metabolism and reduce the variation in bioavailability. The present invention provides application of sublingual pharmaceutical compositions of remdesivir for treating and/or preventing viral infections including coronavirus infections.

BACKGROUND OF THE INVENTION

Remdesivir is known to exhibit antiviral properties. Remdesivir is a single stereoisomer monophosphoramidate prodrug of a nucleoside analog, that is being developed for the treatment of coronavirus disease. Remdesivir is chemically known as 2-Ethylbutyl (2S)-2-{[(S)-{[(2R,3S,4R,5R)-5-(4-aminopyrrolo[2,1-f][1,2,4]triazin-7-yl)-5-cyano-3,4-dihydroxytetra hydrofuran-2-yl] methoxy} (phenoxy) phosphoryl] amino} propanoate. Remdesivir is a white to off-white or yellow non-hygroscopic solid. It is practically insoluble in water and is represented by the following formula as:

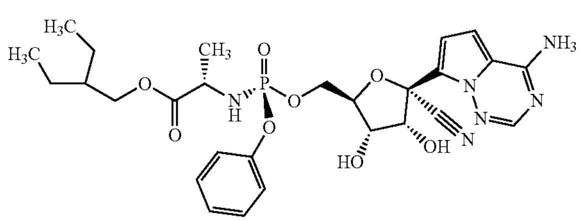 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Remdesivir is a prodrug that metabolizes into its active form GS-441524. GS-441524 is an adenosine nucleotide analog that interferes with the action of viral RNA polymerase and evades proofreading by viral exoribonuclease, causing a decrease in viral RNA production.

Remdesivir is presently approved in many countries in the form of an injectable dosage form in the strength of 100 mg by Gilead Sciences for the treatment of infection caused by coronavirus disease 2019 (COVID-19). Remdesivir is reported to be poorly water soluble, which leads to poor dissolution and poor bioavailability. Moreover, remdesivir is not a first choice for oral delivery as its shows poor hepatic stability, which results in its complete first-pass clearance. These characteristics of remdesivir pose technical challenges to formulation scientists in the development of a suitable oral formulation with desired technical attributes.

PCT Patent Publication No. WO2016/069826 assigned to Gilead Sciences discloses remdesivir as compound. This patent publication also discloses use of remdesivir in the treatment of Filoviridae infection. The publication provides a listing of numerous dosage forms and excipients that may be included in the dosage form along with the numerous compounds disclosed. The patent publication does not appear to recognize the poor solubility of remdesivir or the importance of pH on the compound's solubility. For example, the specification states that the pH of the formulations may range from about 3 to about 11. As such, it is not clear how one of skill in the art can make a soluble and stable solid oral dosage form of remdesivir based on the publication.

US Patent Publication No. US2019/0255085 assigned to Gilead Sciences discloses use of remdesivir in the treatment of Coronaviridae infection in a human. The publication provides a listing of numerous dosage forms and excipients that may be included in the dosage form with the various compounds disclosed. The patent publication does not appear to recognize the poor solubility of remdesivir or the importance of pH on its solubility. For example, the specification states that the pH of the formulations may range from about 3 to about 11. As such, it is not clear how one of skill in the art can make a soluble and stable solid oral dosage form of remdesivir based on the publication.

US Patent Publication No. US2018/346504 assigned to Gilead Sciences discloses crystalline forms of remdesivir. This patent publication further discloses crystalline form I to form IV, mixtures of crystalline forms and maleate form I of remdesivir. Although the publication provides a general listing of dosage forms, the patent publication does not appear to recognize the poor solubility of remdesivir or the importance of pH on its solubility. As such, it is not clear how one of skill in the art can make a soluble and stable solid oral dosage form of remdesivir based on the publication.

US Patent Publication No. US2019/083525 assigned to Gilead Sciences discloses remdesivir injectable dosage form. However, the said patent publication fails to disclose any solid oral composition of remdesivir.

As per the above mentioned literature, development of oral dosage forms of remdesivir is not feasible but instead is challenging due to its adverse physico-chemical properties such as poor solubility and complete first pass metabolism. Many alternative routes of drug administration are available to by-pass first pass metabolism such as ophthalmic, injectable, nasal, transdermal, topical, buccal and sublingual routes. In the sublingual administration, the patient needs to keep the pharmaceutical composition under the tongue while the drug diffuses into the mouth, through the mucosa lining and from there into the bloodstream. As an alternatives of solid oral dosage form or gastrointestinal delivery of drug, sublingual administration might conceivably increase the bioavailability of remdesivir by avoiding first pass hepatic metabolism.

However, rapid absorption of drug by the oral mucosa and low drug loading ability are some of the key requirements for formulation design of sublingual dosage forms. In view of the foregoing, there is an unmet need for improvement in the methods of administering remdesivir so as to increase the bioavailability of the drug and reduce variability in dosing.

The present inventors have successfully designed and developed pharmaceutical compositions of remdesivir suitable for sublingual administration. Further, sublingual delivery of remdesivir is likely to provide more consistent absorption than oral delivery. Further, the process employed in the manufacture of dosage form of remdesivir is consistent and therefore feasible for industrial production. The prepared dosage forms are suitable for treatment of viral infections caused by members of the filoviridae, flaviviridae, paramyxoviridae, orthomyxoviridae, coronaviridae (including COVID-19), arenaviridae and/or adenoviridae families.

SUMMARY OF THE INVENTION

The present invention relates to sublingual pharmaceutical composition comprising remdesivir or its pharmaceutically acceptable salts or solvates thereof and processes for preparing such compositions.

The present invention also relates to sublingual pharmaceutical composition comprising remdesivir or its pharmaceutically acceptable salts or solvates thereof and one or more pharmaceutically acceptable excipients and process for preparing such compositions.

The present invention also relates to sublingual pharmaceutical compositions comprising remdesivir or its pharmaceutically acceptable salts or solvates thereof and one or more pharmaceutically acceptable excipients selected from the group comprising diluent, binder, disintegrant, lubricant, glidant, surfactant, pH regulating agent, effervescent agent, salivating agent, solubilizing agent, stabilizer, sweetener, preservative, flavoring and coloring agent, film forming agent, and solvent or mixtures thereof.

The present invention further relates to sublingual pharmaceutical compositions comprising remdesivir or its pharmaceutically acceptable salts or solvates thereof and one or more pharmaceutically acceptable excipients, which is expected to exhibit desired pharmaceutical technical attributes such as wetting time, pH, disintegration, dissolution, thickness, diameter, hardness, friability, compressibility index, assay, related substance, content uniformity, stability, patient compliance and commercially viable and other requirements also.

The present invention also relates to use of sublingual pharmaceutical compositions comprising remdesivir or its pharmaceutically acceptable salts or solvates thereof in the manufacture of medicament for treating viral infections caused by members of the filoviridae, flaviviridae, paramyxoviridae, orthomyxoviridae, coronaviridae (including COVID-19), arenaviridae and/or adenoviridae families.

DETAILED DESCRIPTION

The present invention can be more readily understood by reading the following detailed description of the invention and study of the included examples.

As used herein, the term "composition", or "dosage form" or "drug delivery system", as in pharmaceutical composition, is intended to encompass a drug product comprising remdesivir and other inert ingredient(s) (e.g., pharmaceutically acceptable excipients). Such pharmaceutical compositions are synonymous with "formulation" and "dosage form" and "composition of the present invention." It can be administered in any pharmaceutical dosage form that can be held in the mouth for a suitable period of time and permits diffusion or erosion of the drug into the mouth cavity where the drug can be absorbed through the mucosa lining of the mouth. Such dosage forms include transmucosal dosage forms, tablets, lozenges, sublingual tablets, sublingual capsule, sublingual film, sublingual aerosol, sublingual solution, sublingual spray, buccal tablets, mucoadhesive tablets, bioadhesive tablets, troches, pastilles, pills, viscous liquids, pastes, drops, gels, patches and the like. "Sublingual administration" may be defined herein as the therapeutic administration of a pharmaceutical composition under the tongue. Preferably, the pharmaceutical composition refers to sublingual tablets. The tablet dosage form as per the present invention can be used for both sublingual or buccal administration or any of them. In another embodiment, the composition can be film-coated or uncoated. In another embodiment, the composition can be scored or unscored tablet. Preferably, the sublingual tablet is unscored. Preferably, the pharmaceutical compositions as per the present invention are intended for immediate or quick release. Preferably, the sublingual tablet compositions as per the present invention dissolve or disperse in the mouth of the subject in from about 1 second to 240 seconds. In a further embodiment, the composition as per the present invention is not an injectable composition and is not intended for parenteral administration.

As used herein, the term "remdesivir" is used in broad sense to include not only "remdesivir" per se (free base) but also its pharmaceutically acceptable salts, solvates, esters, hydrates, isomers, enantiomers, stereoisomers, diastereoisomers, derivatives, metabolites, polymorphs and prodrugs thereof. Polymorph may refer to various crystalline and amorphous forms, which can be characterized by methods such as melting point, X-ray diffraction pattern, Raman spectra, IR spectra or any other method known in the art.

The pharmaceutical compositions of the present invention comprise about 0.1 mg to about 500 mg of remdesivir, preferably about 0.1 mg to about 450 mg, preferably about 0.1 mg to about 400 mg, preferably about 0.1 mg to about 350 mg, preferably about 0.1 mg to about 200 mg, preferably about 0.1 mg to about 100 mg and more preferably about 0.1 mg to about 50 mg remdesivir as described herein. In a further embodiment, compositions of the present invention comprise about 0.1 mg to about 20 mg of remdesivir. The dose may be administered one or more times a day (such as from one to ten times per day).

The term "excipient" means a pharmacologically inactive component such as diluents, binders, disintegrants, lubricants, glidants, surfactants, wetting agents, pH regulating agents, buffers, taste masking agents, water-soluble and/or water dispersible carrier materials, effervescent agents, salivating agents, antioxidants, permeation/penetration enhancers, solubilizing agents, plasticizers, acidulants, polymers, mucoadhesive agents, bioadhesive polymers, stabilizers, emulsifying agents, suspending agents, sweeteners, preservatives, flavoring and coloring agents, film forming agents, mouth feel improvers and solvents and the like. Co-processed excipients are also covered under the scope of present invention. Excipient may be in the form of powder or in the form of dispersion. Combination of excipients performing the same function may also be used to achieve desired formulation characteristics. Excipients may be present in any part (intra and/or extra granular) of the composition in any proportion.

Unless the context requires otherwise, throughout the present specification and claims, the word "comprise" and variations thereof, such as, "comprises" and "comprising" are to be construed in an open, inclusive sense, that is as "including, but not limited to".

As used in this specification, the singular forms "a", "an", and "the" include plural references unless the context clearly dictates otherwise. Thus, for example, a reference to "a process" includes one or more processes, and/or steps of the type described herein and/or which will become apparent to those persons skilled in the art upon reading this disclosure. Unless otherwise stated the weight percentages expressed herein are based on the final weight of the composition. As used herein, the term "about" means±approximately 20% of the indicated value, such that "about 10 percent" indicates approximately 08 to 12 percent.

The term "patient" and/or "subject" are used interchangeably herein. In some embodiments, the patient or subject is a human. In further embodiments, the patient or subject is an animal. In some embodiments, the human can be of any age such as adult, adolescent, paediatric or geriatric.

The term "viral infection" or "virus infection" or "infection" means an infection caused by a virus. The infection may be caused by any virus from filoviridae, flaviviridae, paramyxoviridae, orthomyxoviridae, coronaviridae, arenaviridae and/or adenoviridae families.

Preferably, the infection is a respiratory viral infection. In one embodiment, the respiratory viral infection includes, but is not limited to, influenza viral infection including Influenza A, Influenza B, and Influenza C (seasonal flu), rhinovirus infection (common cold), coronavirus infection caused by alpha, beta, gamma and delta virus families, coronavirus infection (Severe Acute Respiratory Syndrome and common cold), COVID-19, paramyxovirus infection (measles), choriomeningitis virus, junin virus, machupo virus, lassa virus, guanarito virus, sabia, chapare, lujo, lymphocytic choriomeningitis virus, junin virus, machupo virus, lassa virus, guanarito virus, sabia, chapare, lujo, Ebola virus and Marburg virus.

As used herein, the term "therapeutic agent" means an agent or drug utilized to treat, combat, ameliorate, prevent or improve an unwanted condition or allergy or disease or infection of a patient. The composition may be administered, as the case may be, before or after the onset of a viral infection, i.e. for prophylactic or therapeutic treatment purposes, or for both.

The term "stable" refers to the compositions of the present invention, wherein the amount of the active ingredient of a formulation does not deviate from the initial amount by more than the values given in the specification or the guidelines of the common Pharmacopoeias or loss in active ingredient is less than 50% (less than 40%, 30%, 20%, 10%, 5%) of the initial content after being stored for at least 1 month, preferably for at least 2 months, preferably for at least 3 months, more preferably for at least 6 months, more preferably for at least 12 months or more preferably for at least 24 months. The stability of the composition may be evaluated at "long term" conditions 25° C./60% RH, at intermediate condition 30° C./65% RH, at "accelerated conditions" 40° C./75% RH, in the final container either measured as the loss in content of active ingredient. Stability testing may be conducted according to the current guidelines by ICH and FDA. In another embodiment of the invention, there is provided a sublingual tablet composition, wherein the total impurity is less than 5%, less than 3%, less than 2.5%, less than 2%, less than 1.5%, less than 1%, less than 0.9%, less than 0.8%, less than 0.7%, less than 0.6%, or less than 0.5%. In a preferred embodiment of the invention, the total impurity is less than 1% or preferably less than 0.5%.

The present invention relates to transmucosal compositions of remdesivir or its pharmaceutically acceptable salts or solvates thereof.

In one embodiment of the invention, there is provided a sublingual pharmaceutical composition comprising remdesivir or its pharmaceutically acceptable salts or solvates thereof and one or more pharmaceutically acceptable excipients and processes for preparing such compositions.

The present invention also relates to a pharmaceutical composition comprising remdesivir or its pharmaceutically acceptable salts or solvates thereof and one or more pharmaceutically acceptable excipients, wherein the composition is formulated for rapid disintegration in sublingual administration.

In another embodiment of the invention, there is provided a sublingual pharmaceutical composition comprising remdesivir or its pharmaceutically acceptable salts or solvates thereof and one or more pharmaceutically acceptable excipients, which is expected to exhibit desired pharmaceutical technical attributes such as wetting time, pH, disintegration, dissolution, thickness, diameter, hardness, friability, compressibility index, assay, related substance, content uniformity, stability, patient compliance and commercial viability.

In another embodiment of the invention, there is provided a sublingual pharmaceutical composition comprising remdesivir or its pharmaceutically acceptable salts or solvates thereof and one or more pharmaceutically acceptable excipients comprising diluent, binder, disintegrant, surfactant, pH regulating agent, glidant, lubricant, solubilizing agent, sweetener and flavoring agent.

In another embodiment of the invention, the pharmaceutical composition as per the present invention is a sublingual tablet.

In one embodiment, pharmaceutical compositions of the present invention are the solid pharmaceutical compositions which rapidly disintegrate in the mouth of a subject, upon insertion into the buccal cavity or when placed under the tongue. In another embodiment of the invention, there is provided a sublingual tablet composition, wherein the sublingual tablet is intended to disintegrate in a time range of about 1 second to 240 seconds, preferably in about 1 second to 120 seconds or in about 1 second to 60 seconds or within about 30 seconds. Rapid disintegration may include where the pharmaceutical composition is disintegrated in about 1 second to 240 seconds, preferably in about 1 second to 120 seconds or in about 1 second to 60 seconds or within about 30 seconds. Disintegration time testing for tablets can be performed in a United States Pharmacopoeia 43 (USP), tablet disintegration tester wherein a tablet is placed in a basket, which moves upward and downward in a 1 litre beaker of water at 37±2° C.

In another embodiment of the invention, there is provided a sublingual tablet composition, wherein the sublingual tablet exhibits intended wetting time to assess the capacity of the tablets to disintegrate by swelling in water in a time range of from about 1 second to 240 seconds.

In another embodiment of the invention, there is provided a sublingual pharmaceutical composition comprising remdesivir or its pharmaceutically acceptable salts or solvates thereof in an amount of from about 0.1 mg to about 50 mg and one or more pharmaceutically acceptable excipients, wherein the composition has pH between about 2.0 and about 6.5 and is intended to dissolve in about 1 second to about 240 seconds in the mouth of a subject upon placement under the tongue.

In another embodiment of the invention, there is provided a pharmaceutical composition for sublingual administration comprising remdesivir or its pharmaceutically acceptable salts or solvates thereof in an amount from about 0.1 mg to about 50 mg and at least one pH regulating agent, wherein the pH regulating agent is capable to maintain the pH from about 2.0 to about 6.5 to facilitate dissolution of the remdesivir in sublingual mucosa. In another embodiment, the pH regulating agent is capable of maintaining the pH from about 2.0 to about 4.0 to facilitate dissolution of the remdesivir in sublingual mucosa. The pH can be measured by the following method: 1 tablet was disintegrated in 100 mL of purified water and pH was noted down using calibrated pH meter.

In another embodiment of the invention, there is provided a sublingual pharmaceutical composition comprising remdesivir or its pharmaceutically acceptable salts or solvates thereof and pH regulating agent, wherein the ratio of the weight of remdesivir to the weight of the pH regulating agent is from 10:1 to 1:10. In another preferred embodiment, the ratio of remdesivir to pH regulating agent is 2:1 to 10:1. In another preferred embodiment, the ratio of remdesivir to pH regulating agent is 4:1.

The present invention further relates to sublingual pharmaceutical tablet compositions comprising remdesivir or its pharmaceutically acceptable salts or solvates thereof, wherein remdesivir is associated with cyclodextrin in the composition to improve the solubility profile of remdesivir.

In another embodiment of the invention, there is provided a sublingual pharmaceutical composition comprising remdesivir or its pharmaceutically acceptable salts or solvates thereof and solubilizing agent, wherein the ratio of the weight of remdesivir to the weight of the solubilizing agent is from 10:0.5 to 1:10. In another preferred embodiment, the ratio of remdesivir to solubilizing agent is 1:4 to 10:1.

In one embodiment, remdesivir is released 80% or more within 30 minutes or within 20 minutes after administration of the composition. More preferably the composition releases at least 80% drug in 15 minutes or less. More preferably the composition releases not less than 85% drug in 5 minutes. The sublingual tablet compositions prepared by the process as per the present invention can be subjected to in vitro dissolution evaluation according to Test 711 "Dissolution" in the United States Pharmacopoeia 37, United States Pharmacopoeial Convention, Inc., Rockville, Md., 2014 ("USP") to determine the rate at which the active substance is released from the dosage form, and the content of the active substance can be determined in solution by high performance liquid chromatography. In another embodiment, sublingual tablet compositions of the present invention exhibit at least 80% of drug release in 15 minutes or less in 900 ml of 0.1N Hydrochloric Acid, using a USP II apparatus (paddle) at a temperature of 37+0.5° C. and a rotation speed of 50 revolutions per minute.

In another embodiment of the invention, there is provided a pharmaceutical composition in solid form for sublingual administration comprising: remdesivir or its pharmaceutically acceptable salts or solvates thereof in an amount from about 0.1 mg to about 50 mg, a pH regulating agent capable of maintaining the pH from about 2.0 to about 6.5 to facilitate dissolution of the remdesivir in sublingual mucosa and present in an amount such that the ratio of the weight of remdesivir to the weight of the pH regulating agent is from 2:1 to 10:1, and one or more pharmaceutically acceptable excipients, wherein the composition releases at least 80% of the remdesivir in 15 minutes or less when measured in 900 ml of 0.1N Hydrochloric acid using a USP II apparatus (Paddle) at a temperature of 37+0.5° C. and a rotation speed of 50 revolutions per minute.

In another embodiment of the invention, the compositions prepared by the process as per the present invention have a hardness from about 1 to about 70 Newtons (N), and a friability of less than 2% when measured by USP (United States Pharmacopoeia) method. Preferably, the hardness of the tablet according to the present invention is between about 15 N to 30 N. Preferably, the friability of the tablet according to the present invention is not more than 1%. Several devices can be used to test tablet hardness such as a Monsanto tester, a Strong-Cobb tester, a Pfizer tester, an Erweka tester, a Schleuniger tester, etc. Friability can be determined using a Roche friabilator for 100 revolutions at 25 rpm (revolutions per minute). In another embodiment of the invention, there is provided a sublingual tablet composition, which has a thickness of about 2 to about 10 mm. In another embodiment of the invention, there is provided a sublingual tablet composition, which has a diameter of about 2 to about 12 mm, preferably, 3 to 8 mm. In another embodiment of the invention, there is provided a sublingual tablet composition that has a Carr's index in the range of about 1-30%, preferably about 20% value, more preferably about 5% to 15% value, which indicate good flowability.

In another embodiment of the invention, there is provided a sublingual tablet composition of remdesivir, wherein the composition has the assay in the range from 90% to 110% as measured by HPLC (High Performance Liquid Chromatography) method using a suitable column (such as Zorbax SB-C18).

In another embodiment of the invention, content uniformity of the sublingual composition is within acceptable limits and meets the requirements for dosage uniformity, in the acceptance value less than or equal to 15% as measured by suitable technique such as HPLC (High Performance Liquid Chromatography) method.

In another embodiment, the sublingual tablet composition comprises: a) about 0.1% to about 97% of remdesivir or its pharmaceutically acceptable salts or solvates thereof, and b) about 0.1% to about 90% of one or more pharmaceutically acceptable excipients.

In another embodiment of the invention, the sublingual composition comprises: a) from about 0.1% to about 97% by weight of remdesivir or its pharmaceutically acceptable salts or solvates thereof, b) from about 0 to about 70% by weight of one or more diluents, c) from about 0 to about 30% by weight of one or more binders, d) from about 0 to about 20% by weight of one or more disintegrants, e) from about 0 to about 50% by weight of one or more carriers, f) from about 0 to about 5% by weight of one or more surfactants, g) from about 0 to about 5% by weight of one or more glidants, h) from about 0 to about 5% by weight of one or more pH regulating agents, i) from about 0 to about 30% by weight of one or more solubilizing agents, j) from about 0.1% to about 5% by weight of one or more lubricants, k) from about 0 to about 5% by weight of one or more preservatives, l) from about 0.1% to about 5% by weight of one or more sweeteners, m) from about 0 to about 20% by weight of one or more bio/mucoadhesive agents, and optionally, n) one or more other pharmaceutically acceptable excipients.

In another embodiment of the invention, the sublingual composition comprises: a) from about 5% to about 85% by weight of remdesivir or its pharmaceutically acceptable salts or solvates thereof, b) from about 30% to about 60% by weight of one or more diluents, c) from about 0 to about 20% by weight of one or more binders, d) from about 0 to about 10% by weight of one or more disintegrants, e) from about 0 to about 30% by weight of one or more carriers, f) from about 0 to about 2% by weight of one or more surfactants, g) from about 0 to about 2% by weight of one or more glidant, h) from about 0 to about 5% by weight of one or more pH regulating agents, i) from about 0 to about 30% by weight of one or more solubilizing agents, j) from about 0.1% to about 2% by weight of one or more lubricants, k) from about 0.1% to about 2% by weight of one or more preservatives, l) from about 0.1% to about 2% by weight of one or more sweeteners, m) from about 0 to about 10% by weight of one or more bio/mucoadhesive agents, and optionally n) one or more other pharmaceutically acceptable excipients.

In another embodiment of the invention, the sublingual composition comprises: a) from about 0.1% to about 85% by weight of remdesivir or its pharmaceutically acceptable salts or solvates thereof, b) from about 20% to about 70% by weight of one or more diluents, c) from about 0.1% to about 10% by weight of one or more binders, d) from about 0.1% to about 15% by weight of one or more disintegrants, e) from about 0.01% to about 3% by weight of one or more surfactants, f) from about 0.01% to about 3% by weight of one or more glidants, g) from about 0.01% to about 10% by weight of one or more pH regulating agents, h) from about 0.01% to about 3% by weight of one or more lubricants, i) from about 0.01% to about 5% by weight of one or more sweeteners, and optionally j) one or more other pharmaceutically acceptable excipients.

In another embodiment of the invention, the sublingual tablet composition comprises: a) from about 0.1% to about 35% by weight of remdesivir or its pharmaceutically acceptable salts or solvates thereof, b) from about 20% to about 70% by weight of one or more diluents, c) from about 0.1% to about 5% by weight of one or more binders, d) from about 0.1% to about 10% by weight of one or more disintegrants, e) from about 0.01% to about 3% by weight of one or more surfactants, f) from about 0.01% to about 3% by weight of one or more glidants, g) from about 0.01% to about 5% by weight of one or more pH regulating agents, h) from about 0.01% to about 3% by weight of one or more lubricants, i) from about 0.01% to about 5% by weight of one or more sweeteners, and optionally j) one or more other pharmaceutically acceptable excipients.

In another embodiment of the invention, the sublingual composition comprises: a) from about 0.1% to about 85% by weight of remdesivir or its pharmaceutically acceptable salts or solvates thereof, b) from about 20% to about 70% by weight of one or more diluents, c) from about 0.1% to about 10% by weight of one or more binders, d) from about 0.1% to about 15% by weight of one or more disintegrants, e) from about 0.01% to about 3% by weight of one or more glidants, f) from about 0.01% to about 20% by weight of one or more solubilizing agents, g) from about 0.01% to about 3% by weight of one or more lubricants, h) from about 0.01% to about 5% by weight of one or more sweeteners, and optionally i) one or more other pharmaceutically acceptable excipients.

In another embodiment of the invention, the sublingual tablet composition comprises: a) from about 0.1% to about 35% by weight of remdesivir or its pharmaceutically acceptable salts or solvates thereof, b) from about 20% to about 70% by weight of one or more diluents, c) from about 0.1% to about 5% by weight of one or more binders, d) from about 0.1% to about 10% by weight of one or more disintegrants, e) from about 0.01% to about 3% by weight of one or more glidants, f) from about 0.01% to about 20% by weight of one or more solubilizing agents, g) from about 0.01% to about 3% by weight of one or more lubricants, h) from about 0.01% to about 5% by weight of one or more sweeteners, and optionally i) one or more other pharmaceutically acceptable excipients.

In another embodiment of the invention, the sublingual tablet composition comprises: a) from about 0.1% to about 35% by weight of remdesivir or its pharmaceutically acceptable salts or solvates thereof, b) from about 20% to about 70% by weight of one or more diluents, c) from about 0.1% to about 5% by weight of one or more binders, d) from about 0.1% to about 10% by weight of one or more disintegrants, e) from about 0.01% to about 3% by weight of one or more glidants, f) from about 0.01% to about 20% by weight of one or more solubilizing agents, g) from about 0.01% to about 5% by weight of one or more pH regulating agents, h) from about 0.01% to about 3% by weight of one or more lubricants, i) from about 0.01% to about 5% by weight of one or more sweeteners, and optionally j) one or more other pharmaceutically acceptable excipients.

In another embodiment of the invention, the diluent comprises one or more of mannitol, lactose, microcrystalline cellulose, silicified microcrystalline cellulose, sucrose, starch, pregelatinized starch, xylitol, sorbitol, maltodextrin, polydextrose, isomalt, or mixtures thereof.

In another embodiment of the invention, the pH regulating agent comprises one or more of organic acids (such as citric acid), inorganic acids (such as hydrochloric acid, sulphuric acid, phosphoric acid, or hydrobromic acid), basic amino acids or mixtures thereof. In a preferred embodiment, the pH regulating agent comprises one or more of citric acid, tartaric acid, oxalic acid, hydrochloric acid, or mixtures thereof.

In another embodiment of the invention, the one or more solubilizing agents are selected from the group comprising cyclodextrin (cyclodextrin analogs, such as but not limited to, alpha-, beta- and gamma-cyclodextrin analogs and their derivatives), sodium lauryl sulfate, hydroxypropylmethylcellulose, hydroxypropylcellulose, sodium carboxymethylcellulose, povidone, or mixtures thereof.

In another embodiment of the invention, there is provided a sublingual pharmaceutical composition comprising remdesivir or its pharmaceutically acceptable salts or solvates thereof and one or more pharmaceutically acceptable excipients, wherein remdesivir has a particle size distribution $D_{90}$ less than about 200 µm, $D_{50}$ less than about 100 µm and $D_{10}$ less than about 50 µm.

In another embodiment of the invention, the sublingual pharmaceutical composition is prepared by wet granulation (rapid mixture granulation, fluid bed granulation, spray drying), dry granulation, dry blending, dry mixing and direct compression. Other formulation techniques are also contemplated within the scope of the present invention such as extrusion-spheronization, hot melt extrusion, freeze-drying, spray drying, mass extrusion and molding. In a preferred embodiment of the present invention, the composition is prepared by wet granulation process.

In another embodiment of the invention, the solvent used in the preparation of the composition is selected from the group comprising aqueous solvent, alcoholic solvent, hydroalcoholic solvent, acidic solvent, ether solvent or any mixtures thereof. In a preferred embodiment, one or more solvents used in the preparation of the composition are selected from the group comprising ethanol, water, tetrahydrofuran, hydrochloric acid or any mixtures thereof in any volume ratio.

In another embodiment of the invention, there is provided a process of preparing sublingual tablet compositions that includes the steps of: a) sifting the accurately weighed quantities of one or more pharmaceutically acceptable excipient(s) such as diluent and pH regulating agent through a suitable sieve, b) preparing a solution or dispersion of drug in suitable solvent (such as ethanol or tetrahydrofuran or their mixtures), c) dissolving a suitable surfactant in suitable solvent (preferably water) and then adding suitable binder in that solution, d) granulating the mixture of step a) with a solution or dispersion of step b) followed by granulation with solution or dispersion of step c), e) drying the granulated mass, optionally milling of the dried granules, f) blending of dried granules with one or more pharmaceutically acceptable excipient(s) such as suitable disintegrant, glidant, sweetener, and optional flavor, and passing through a suitable sieve, g) lubricating the sifted blend of step and passing through a suitable sieve, and h) compressing the lubricated granules into tablets.

In another embodiment of the invention, there is provided a process of preparing a sublingual tablet composition that includes the steps of: a) sifting the accurately weighed quantities of one or more pharmaceutically acceptable excipient(s) such as one or more of diluent, disintegrant, binder and glidant through a suitable sieve, b) preparing a solution of solubilizing agent in 1N hydrochloric acid followed by addition of suitable solvent (such as ethanol), c) dissolving the drug in the solution as prepared in step b), followed by pH adjustment with 1N hydrochloric acid at suitable pH (such as between pH 2 to pH 4), d) granulating the mixture of step a) with a solution of step c), e) sifting the wet mass through a suitable sieve, f) drying the wet granules, and sifting through a suitable sieve, g) blending of dried granules with suitable disintegrant, glidant, sweetener, and optional flavor, and sifting through a suitable sieve, h) lubricating the sifted blend of step g) and passing through a suitable sieve, i) compressing the lubricated granules into tablets.

In another embodiment of the invention, there is provided a sublingual pharmaceutical composition comprising remdesivir or its pharmaceutically acceptable salts or solvates thereof and one or more pharmaceutically acceptable excipients, wherein the composition is stable.

In another embodiment, the present invention includes a sublingual pharmaceutical composition comprising remdesivir or its pharmaceutically acceptable salts or solvates thereof and one or more pharmaceutically acceptable excipients, wherein the composition is free of other polymorphic forms or any polymorphic form conversion.

In another embodiment of the invention, the pH regulating agent is selected such that the degradation of active ingredient or other components of the composition is slowed or reduced, as compared to a composition in which the pH regulating agent is not present. For example, the pH regulating agent may at least help in preventing significant degradation of the composition after a certain period of shelf life. The present inventors have surprisingly observed that the sublingual composition is stable in pH range from about 2 to about 6.5. The present inventors have further observed that at pH higher than 6.5 (such as at pH 7, 7.5 or above) there was a significant increase (more than 10%) in impurities in the composition due to instability of the active ingredient.

In one embodiment, the sublingual pharmaceutical compositions as per the present invention provides a method of increasing the bioavailability of remdesivir. More particularly, sublingual pharmaceutical compositions as per the present invention allow the active agent to by-pass first pass metabolism, thereby enhancing the bioavailability of the active agent. Such sublingual compositions can offer several advantages over other modes of drug delivery, including, but not limited to, increased chemical stability of the active ingredient, sufficient shelf-life, good pharmacotechnical properties, stable drug release, increasing the onset of action, lowering the required dosage, enhancing the efficacy and improving the safety profile of the active agent.

Bioavailability refers to the proportion of the drug administered that reaches the physiological site where the drug exerts its therapeutic effect, which is generally regarded as the blood stream for many drugs. The bioavailability of a drug is most readily expressed as the concentration of the drug or its active metabolites in the blood plasma integrated over time. This quantity is commonly referred to as the "area under the curve" or "AUC". Sublingual administration of remdesivir according to this invention preferably increases the drug's bioavailability at least 5% or more, 10% or more, 20% or more, 30% or more, 40% or more, or 50% or more as compared to oral administration. In a further embodiment, relative bioavailability studies can be performed to compare the bioavailability of the sublingual tablet formulation with an injection (intravenous) dosage form.

In one embodiment, the present invention provides use of sublingual pharmaceutical compositions of the present invention in methods for treating, preventing, ameliorating, and/or delaying the onset of one or more symptoms associated with or resulting from a viral infection, preferably a respiratory viral infection in a subject, caused by members of the filoviridae, flaviviridae paramyxoviridae, orthomyxoviridae, coronaviridae, arenaviridae or adenoviridae families. In an embodiment, the viral infection is a coronavirus infection. In an another embodiment, the present invention provides use of sublingual pharmaceutical compositions of the present invention in the treatment of COVID-19 infection.

In certain embodiments, the subject or patient is a human. In certain embodiments, the subject or patient is an adult. In certain embodiments, the subject or patient is an adolescent. In certain embodiments, the subject or patient is a child. In one embodiment, the subject or patient is of age group between one-year-old to 90 years old.

In one embodiment, the symptoms or complications associated with viral infection or respiratory infection include, but are not limited to, chill, fever (mild or high fever), headache, sweating, fatigue, tiredness, sneezing, dry cough, sore throat, runny nose, vomiting, dehydration, cough with mucus, body aches, abdominal pain, joint pain, chest pain or discomfort, diarrhea, breathing problem or shortness, pneumonia, asthma, bronchitis, chronic obstructive pulmonary disease, congestive heart failure and/or any other symptoms or complications provided herein elsewhere.

In one embodiment, the composition can be administered once daily, or divided into multiple daily doses from once per day to once in six months such as twice daily, three times daily, four times daily, once a week, twice in week, thrice in week, once in two weeks, once in three weeks, once in four weeks or the like. In one embodiment, the composition is intended for at least once daily administration.

In another embodiment, sublingual pharmaceutical compositions of the present invention may be packaged in HDPE bottles or glass bottles or blister packs. Packaging material may optionally contain desiccants. The packaging material used according to the present invention favorably protects the composition from air, light and moisture. Further, the composition of the present invention is packaged into a suitable pack together with instructions to place the dosage form under a patient's tongue or in the buccal cavity.

Any pharmaceutically acceptable granulating agent can be used for wet granulation. Preferable granulating solvents include, but are not limited to, aqueous, non-aqueous, alcoholic, hydro-alcoholic, ether, acidic solvents as a granulating liquid such as water, esters such as ethyl acetate, ketones such as acetone, alcohols such as methanol, ethanol (including ethanol 95%), isopropanol, butanol, dichloromethane, chloroform, dimethyl acetamide, dimethyl sulfoxide, ether (such as tetrahydrofuran, methyl tert-butyl ether, 1,4-dioxane and combinations thereof), diethyl ether, hydrochloric acid (such as 1N hydrochloric acid), mixtures of one or more alcohols and water and any combinations or mixtures thereof. In a further embodiment, solvents used as per the present invention are mixtures of one or more alcohol and water, in various volume ratios. In some embodiment, suitable organic or inorganic acids selected from the group comprising citric acid, malic acid, fumaric acid, tartaric acid and hydrochloric acid can also be added in granulation process or in granulation solution. In one embodiment, the solvent is a mixture of ethanol and hydrochloric acid (preferably 1N hydrochloric acid) in 50:50 ratios.

Various useful fillers or diluents include, but are not limited to, microcrystalline cellulose ("MCC"), sodium alginate, silicified MCC, microfine cellulose, lactitol, cellulose acetate, kaolin, glucose, lactose, maltose, fructose, sucrose, trehalose, starch, pregelatinized starch (PGS), sugar alcohols such as mannitol, D-mannitol, xylitol, maltitol, sorbitol, dextrates, dextrin, maltodextrin, compressible sugar, confectioner's sugar, dextrose, polydextrose, simethicone, calcium carbonate, calcium sulfate, calcium phosphate, dibasic calcium phosphate, tribasic calcium phosphate, magnesium carbonate, magnesium oxide, isomalt, mixture of microcrystalline cellulose and mannitol or any mixtures thereof. The amount of diluent according to the present invention ranges from about 0 to about 90% by weight of composition. In an embodiment, the diluent according to the present invention is present in an amount of about 90% or less, 80% or less, e.g. 70% or less, 60% or less, 50% or less, 40% or less, 30% or less, 20% or less.

Various useful binders include, but are not limited to, acacia, guar gum, xanthan gum, alginic acid, sodium alginate, dextrin, carbomer, maltodextrin, methylcellulose, ethyl cellulose, hydroxyethyl cellulose, hydroxypropyl cellulose (HPC), hydroxypropyl methylcellulose (HPMC), hydroxyethylmethyl cellulose, carboxymethyl cellulose sodium, cottonseed oil, povidone (PVP), ceratonia, dextrose, polydextrose, starch, gelatin, pregelatinized starch, hydrogenated vegetable oil type I, maltodextrin, microcrystalline cellulose, polyethylene oxide, polymethacrylates and mixtures thereof. Binder can be present in powder form or as a dispersion or mixture of both, in intra and/or extra granular part of the composition. The amount of binder according to the present invention ranges from about 0 to about 50% by weight of composition. In an embodiment, the binder according to the present invention is present in an amount of about 50% or less, 40% or less, e.g. 30% or less, 20% or less, 10% or less, 5% or less.

Various useful disintegrants and/or super-disintegrants include, but are not limited to, croscarmellose sodium, carboxymethyl cellulose sodium, carboxymethyl cellulose calcium, povidone, crospovidone, polacriilin potassium, sodium starch glycolate, alginic acid, sodium alginate, calcium phosphate, colloidal silicon dioxide, docusate sodium, guar gum, low substituted hydroxypropyl cellulose, magnesium aluminum silicate, methylcellulose, microcrystalline cellulose, silicified microcrystalline cellulose, starch, pregelatinized starch and/or combinations thereof. The disintegrant can be present in intra-granular or extra-granular part or in both (intra and extra granular) parts of the composition. The amount of disintegrant according to the present invention ranges from about 0 to about 40% by weight of composition. In an embodiment, the disintegrant according to the present invention is present in an amount of about 40% or less, 30% or less, e.g. 20% or less, 10% or less.

Pharmaceutically acceptable lubricants include, but are not limited to, stearic acid, zinc stearate, sucrose stearate, sodium benzoate, hydrogenated vegetable oil, calcium stearate, adipic acid, glyceryl palmitostearate, glycerine monostearate, medium-chain triglycerides, glyceryl behenate, sodium lauryl sulphate, sodium stearyl fumarate, magnesium lauryl sulphate, magnesium stearate, polyethylene glycol. The amount of lubricant according to the present invention ranges from about 0 to about 20% by weight of composition. In an embodiment, the lubricant according to the present invention is present in an amount of about 20% or less, e.g. 10% or less, 5% or less.

Various useful effervescent agents include, but are not limited to, food acids and acids such as tartaric acid, fumeric acid, citric acid, succinic acid, amalic, adipic, sodium bicarbonate, sodium carbonate, potassium carbonate, potassium bicarbonate, magnesium carbonate and or like compounds. The amount of effervescent agents according to the present invention ranges from about 0 to about 90% by weight of the composition. In an embodiment, the effervescent agents according to the present invention are present in an amount of about 90% or less, 80% or less, e.g. 70% or less, 60% or less, 50% or less, 40% or less, 30% or less, 20% or less, 10% or less.

Various useful surfactants include, but are not limited to, sodium lauryl sulphate, polysorbate (e.g. polysorbate 20, polysorbate 40, polysorbate 60, and polysorbate 80), cetrimide, cetyl alcohol, stearyl alcohol, cetyl stearyl alcohol, cholesterol, polyethylene glycols, polyglycerin fatty acid esters such as decaglyceryl monolaurate and decaglyceryl monomyristate, sorbitan fatty acid esters such as sorbitan monostearate, polyoxyethylene sorbitan fatty acid ester such as polyoxyethylene sorbitan monooleate, polyoxyethylene alkyl ether such as polyoxyethylene lauryl ether, polyoxyethylene castor oil, polyoxyethylenepolyoxypropylene block copolymers such as poloxamer (such as poloxamer 124, poloxamer 188, poloxamer 237, poloxamer 338, and poloxamer 407), and combinations thereof. The amount of surfactant according to the present invention ranges from about 0 to about 30% by weight of the composition. In an embodiment, the surfactant according to the present invention is present in an amount of about 30% or less, e.g. 20% or less, 10% or less, 5% or less, or 2% or less.

Suitable pH regulating agents include, but are not limited to, disodium hydrogen phosphate, sodium dihydrogen phosphate and the equivalent potassium salt, alkaline oxides (potassium oxide, sodium oxide, barium oxide, magnesium oxide and aluminium oxide), sodium hydroxide, potassium hydroxide, calcium hydroxide, calcium oxide, citrate, phosphate, borate salts, organic and inorganic acids such as citric acid, lactic acid, acetic acid, formic acid, oxalic acid, uric acid, malic acid, tartaric acid, succinic acid, benzoic acid, sorbic acid, ascorbic acid, phosphoric acid, boric acid, hydrochloric acid, sulphuric acid, nitric acid, phosphoric acid, hydrobromic acid, hydroiodic acid or hydrofluoric acid, as known in the art such as those described above, carbonate salts (sodium carbonate, potassium carbonate, calcium carbonate, ammonium carbonate, or magnesium carbonate), bicarbonate salts (sodium bicarbonate, potassium bicarbonate, calcium bicarbonate, ammonium bicarbonate, or magnesium bicarbonate), basic amino acids (arginine, histidine, lysine, glycine), and amino sugars (N-acetylglucosamine, galactosamine, glucosamine, sialic acid, or meglumine). Binary buffer systems are also included in the ambit of the present invention. The amount of pH regulating agents according to the present invention ranges from about 0 to about 20% by weight of composition. In an embodiment, the pH regulating agents according to the present invention are present in an amount of about 20% or less, e.g. 10% or less, 5% or less, 3% or less.

Suitable glidants include, but are not limited to, calcium silicate, magnesium silicate, magnesium trisilicate, stearic acid and its derivatives or esters like magnesium stearate, calcium stearate and sodium stearate and the corresponding esters such as sodium stearyl fumarate, talc, colloidal silicon dioxide, tribasic calcium phosphate, starch, starch derivatives or mixtures thereof. The amount of glidant according to the present invention ranges from about 0 to about 20% by weight of composition. In an embodiment, the glidant according to the present invention is present in an amount of about 20% or less, e.g. 10% or less, 5% or less, 3% or less.

Various useful salivating agents include, but are not limited to, alkyl aryl sulfonates, alkyl sulfonates, alkyl sulfates, sulfonated amides and amities, sulfated and sulfonated esters and ethers, mono-, di-, and triglycerides, diacetyl tartaric esters of monoglycerides, polyglycerol esters, sorbitan esters and ethoxylates, lactylated esters, phospholipids such as lecithin, polyethoxylated esters, polyoxyethylene sorbitan esters, propylene glycol esters, sucrose esters, citric acid, malic acid, tartarate, sodium chloride, potassium chloride, and mixtures thereof. The amount of salivating agents according to the present invention ranges from about 0 to about 30% by weight of composition. In an embodiment, the salivating agents according to the present invention are present in an amount of about 30% or less, e.g. 20% or less, 10% or less, 5% or less, or 2% or less.

Various useful solubilizing agents, permeation/penetration enhancers include, but are not limited to, alcohols, polyethylene glycols, cyclodextrins (cyclodextrin analogs, such as but not limited to, alpha-, beta-, and gamma-cyclodextrin analogs and their derivatives such as sulfobutyl-ether-β-cyclodextrin (SBECD)), sodium lauryl sulfate, hydroxypropylmethylcellulose, hydroxypropylcellulose, sodium carboxymethylcellulose, povidone, sucrose laurate or sucrose oleate, sodium dodecyl sulfate (SDS) or palmitoyl carnitine chloride (PCC) and citric acid. The amount of solubilizing agents, permeation/penetration enhancers according to the present invention ranges from about 0 to about 30% by weight of composition. In an embodiment, the solubilizing agent, permeation enhancer according to the present invention is present in an amount of about 30% or less, 20% or less, 10% or less, e.g. 5% or less, 3% or less, 2% or less, or 1% or less.

Various useful preservatives include, but are not limited to, citric acid, butylated hydroxyanisole, vitamin C, vitamin E, parabens (methyl paraben, propyl paraben), phenylethyl alcohol, sorbic acid, benzyl alcohol, alkylbenzyldimethylammonium chloride with a chain length of from $C_8$ to $C_{18}$ in the alkyl moiety, m-cresol or alkyl-4-hydroxybenzoate. The amount of preservatives according to the present invention ranges from about 0 to about 20% by weight of composition. In an embodiment, the preservatives according to the present invention are present in an amount of about 20% or less, e.g. 10% or less, 5% or less, 3% or less.

Various useful flavoring agents include, but are not limited to, mint powder, menthol, vanillin, aspartame, acesulfame potassium, saccharin sodium, aromatics and/or natural oils, synthetic flavor oils, extracts from plants, leaves, flowers, fruits and combinations thereof, commercially available orange, grape, cherry and bubble gum flavors, tutti-frutti flavors and mixtures thereof. The amount of flavoring agents according to the present invention ranges from about 0 to about 10% by weight of composition. In an embodiment, the flavoring agents according to the present invention are present in an amount of about 10% or less, e.g. 5% or less, 3% or less, 2% or less, or 1% or less.

Various useful sweetening agents include, but are not limited to, sugars such as sucrose, sucralose, glucose, dextrose, maltose, fructose, artificial sweeteners (such as saccharin, saccharin sodium, aspartame, acesulfame, acesulfame potassium, neohesperidine dihydrochalcone, monoammonium glycyrrhizinate, sugar alcohols (such as mannitol, xylitol, lactitol, maltitol syrup) and mixtures thereof, present conveniently in an amount of from about 0 to about 65% by weight of the composition. In an embodiment, the sweetening agents according to the present invention is in an amount of about 65% or less, e.g. 60% or less, 50% or less, 40% or less, 30% or less, 20% or less, 10% or less, 5% or less, 3% or less, 2% or less, or 1% or less.

Various other excipients or inert ingredients such as antioxidants, acidulants, effervescent agents, water-soluble and/or water dispersible carrier materials, bio/mucoadhesion promoting agents, stabilizers, emulsifiers, plasticizers, suspending agents and coloring agents are also covered under the ambit of the present invention. The amount of these excipients according to the present invention may range from about 0 to about 90% by weight of the composition. In an embodiment, these excipients according to the present invention are present in an amount of about 90% or less, 80% or less, e.g. 70% or less, 60% or less, 50% or less, 40% or less, 30% or less, 20% or less, 10% or less.

The invention is further defined by reference to the following examples describing in detail the methods for the preparation and testing of remdesivir pharmaceutical compositions. The following examples are provided to illustrate embodiments of the disclosure but they are by no means intended to limit its scope.

EXAMPLES

Remdesivir sublingual tablets were prepared by using the quantitative formula as given in Tables 1, 2 and 3 (Quantity/Tablet (% w/w))

TABLE 1

Examples 1-2:

| S. No. | Ingredient | Function | 1 | 2 |
|---|---|---|---|---|
| 1. | Remdesivir | Drug | 0.1-97 | 5-85 |
| 2. | Mannitol/Sorbitol/Xylitol | Diluent | 0-70 | 30-60 |
| 3. | HPMC/HPC/PVP | Binder | 0-30 | 0-20 |
| 4. | Sodium starch glycolate/Croscarmellose sodium/PGS | Disintegrant | 0-20 | 0-10 |
| 5. | Gelatin/Sodium alginate | Carrier | 0-50 | 0-30 |
| 6. | Sodium Lauryl Sulphate/Polysorbate 80/Poloxamer | Surfactant | 0-5 | 0-2 |
| 7. | Citric acid | pH adjusting/salivating agent/solubilizer | 0-5 | 0-5 |
| 8. | Talc/Colloidal silicon di-oxide | Glidant | 0-5 | 0-2 |
| 9. | Magnesium Stearate | Lubricant | 0.1-5 | 0.1-2 |
| 10. | Butylated Hydroxyanisole | Preservative/Antioxidant | 0-5 | 0.1-2 |
| 11. | Sucralose/Saccharin Sodium/Aspartame | Sweetener | 0.1-5 | 0.1-2 |

TABLE 1-continued

Examples 1-2:

| S. No. | Ingredient | Function | 1 | 2 |
|---|---|---|---|---|
| 12. | Milk Protein Concentrate | Bio/Mucoadhesive | 0-20 | 0-10 |
| 13. | Aqueous or Alcoholic or Acidic solvent or any mixture thereof | Solvent | q.s. | q.s. |

Procedure: Wet granulation.

TABLE 2

Examples 3-9:

| S. No. | Ingredient | Function | 3 | 4 | 5 | 6 | 7 | 8 | 9 |
|---|---|---|---|---|---|---|---|---|---|
| 1. | Remdesivir | Drug | 0.1-85 | 20 | 19.4 | 20 | 20 | 13.3 | 13.3 |
| 2. | Mannitol | Diluent | 20-70 | 63.8 | 59.5 | 53.8 | 58.3 | 64.9 | 67.9 |
| 3. | PVP | Binder | 0.1-10 | 1 | 1 | 1 | 1 | 1 | 1 |
| 4. | Crospovidone | Disintegrant | 0.1-15 | 4 | 7.8 | 7 | 8 | 8 | 5 |
| 5. | Poloxamer | Surfactant | 0.01-3 | 2 | 1.9 | 2 | 2 | 2 | 2 |
| 6. | Citric acid | pH regulating agent | 0.01-10 | 5 | 4.9 | 5 | 5 | 5 | 5 |
| 7. | Colloidal silicon di-oxide | Glidant | 0.01-3 | 1.5 | 2.9 | 3 | 3 | 3 | 3 |
| 8. | Magnesium Stearate | Lubricant | 0.01-3 | 2.3 | 2.2 | 2.3 | 2.3 | 2.3 | 2.3 |
| 9. | Acesulfame Potassium | Sweetener | 0.01-5 | 0.5 | 0.5 | 5 | 0.5 | 0.5 | 0.5 |
| 10. | Flavor (mint) | Flavoring agent | — | — | — | — | 1 | — | — |
| 11. | Solvent (Ethanol) | Solvent | q.s. | q.s. | q.s. | q.s. | — | q.s. | q.s. |
| 12. | Solvent (Water) | Solvent | q.s. | q.s. | q.s. | q.s. | — | — | — |
| 13. | Solvent (Tetrahydrofuran) | Solvent | — | — | — | — | q.s. | q.s. | q.s. |

TABLE 3

Examples 10-14:

| S. No. | Ingredient | Function | 10 | 11 | 12 | 13 | 14 |
|---|---|---|---|---|---|---|---|
| 1. | Remdesivir | Drug | 20 | 13.3 | 0.7 | 6.7 | 33.3 |
| 2. | Mannitol | Diluent | 63.8 | 28.7 | 28.7 | 28.7 | 28.7 |
| 3. | Microcrystalline cellulose | Diluent | — | 26.4 | 39.1 | 33.1 | 6.4 |
| 4. | Beta Cyclodextrin | Solubilizing agent | 2 | 13.3 | 13.3 | 13.3 | 13.3 |
| 5. | PVP | Binder | 1 | 0.7 | 0.7 | 0.7 | 0.7 |
| 6. | Crospovidone | Disintegrant | 4 | 8 | 8 | 8 | 8 |
| 7. | Citric acid | pH regulating agent | 5 | — | — | — | — |
| 8. | Colloidal silicon dioxide | Glidant | 1.5 | 3 | 3 | 3 | 3 |
| 9. | Magnesium Stearate | Lubricant | 2.3 | 2.3 | 2.3 | 2.3 | 2.3 |
| 10. | Acesulfame Potassium | Sweetener | 0.5 | 3.3 | 3.3 | 3.3 | 3.3 |
| 11. | Flavor (mint) | Flavoring agent | — | 1 | 1 | 1 | 1 |
| 12. | Solvent (Ethanol) | Solvent | q.s. | q.s. | q.s. | q.s. | q.s. |
| 13. | Solvent (Water) | Solvent | q.s. | — | — | — | — |
| 14. | 1N HCl | Solvent/pH regulating agent | — | q.s. | q.s. | q.s. | q.s. |

Procedure I—Table 2: i) Diluent and pH regulating agent were sifted through a suitable sieve, ii) drug was dispersed in to a suitable solvent (such as ethanol or mixtures with other solvents), iii) surfactant was dissolved in suitable solvent (such as water) followed by addition of binder, iv) step i) blend was granulated using dispersion of step ii) followed by solution of step iii), v) wet granules were dried followed by passing the dried granules through a suitable sieve, vi) dried granules were blended with suitable excipients such as sweetener, disintegrant, glidant, flavor (optional) and lubricant and were sifted through a suitable sieve, vii) the blend of step vi) was compressed into tablets using suitable punches.

Procedure II—Table 3: i) One or more diluents, disintegrant, binder and glidant were sifted through a suitable sieve, ii) solubilizing agent was dissolved in suitable solvent (such as 1N hydrochloric acid) followed by addition of another suitable solvent (such as ethanol), iii) drug was dissolved in solution as prepared in step ii), followed by pH adjustment with 1N hydrochloric acid at suitable pH (such as between pH 2 to pH 4), iv) step i) blend was granulated using solution of step iii), v) wet mass was sifted through a suitable sieve, vi) wet granules were dried and sifted through a suitable sieve, vii) dried granules were blended with suitable disintegrant, glidant, sweetener, flavor (optional) and lubricant and sifted through a suitable sieve and added to step vi) granules, viii) the blend of step viii) was compressed into tablets using suitable punches.

Results: Dissolution: The dissolution profile of sublingual tablet compositions prepared using quantitative compositions, as given below in Table 4 was measured in 900 ml of 0.1N Hydrochloric acid using a USP II apparatus (Paddle) at a temperature of 37+0.5° C. and a rotation speed of 50 revolutions per minute. Quantitative composition as given below in Table 4 exhibited at least 80% of drug release in 15 minutes or less, accordingly the dissolution profiles of all of the formulations were found to be acceptable.

TABLE 4

| Time Point | % Drug release | | | | | | | |
|---|---|---|---|---|---|---|---|---|
| (mm.) | 5 | 7 | 8 | 9 | 11 | 12 | 13 | 14 |
| 5 | 98 | 92 | 92 | 89 | 87 | 67 | 61 | 57 |
| 10 | 98 | 92 | 93 | 91 | 93 | 90 | 87 | 80 |
| 15 | 100 | 92 | 92 | 89 | 95 | 88 | 91 | 89 |
| 30 | 100 | 92 | 92 | 89 | 95 | 89 | 92 | 94 |

The pH results are provided below in Table 5.

TABLE 5

| pH Results: | | | | | | | | | | |
|---|---|---|---|---|---|---|---|---|---|---|
| Example No. | | | | | | | | | | |
| | 4 | 5 | 6 | 7 | 8 | 9 | 10 | 11 | 12 | 13 14 |
| pH | 3.8 | 3.7 | 3.7 | 3.8 | 3.7 | 3.6 | 3.7 | 3.8 | | 2-6.5 |

The measurement of related substances are provided in Table 6.

TABLE 6

| Related Substance: | |
|---|---|
| Example No. | |
| 4 5 6 7 8 9 10 11 12 13 14 | |
| Related Substance (as measured by HPLC) | Less than 2% |

Additional measurements of the physical characteristics of the tablets are provided in Table 7.

TABLE 7

| Other Results: | | | | | | | |
|---|---|---|---|---|---|---|---|
| Example No. | | | | | | | |
| | 4 | 5 | 6 | 7 | 8 | 9 | 10 | 11 |
| Hardness | 18-20 | 19-22 | 24-26 | 19-22 | 20-25 | 20-25 | 18-20 | 22-25 |
| Friability | NMT 1% | | | | | | | |
| Particle Size | $D_{90}$ less than about 200 pm | | | | | | | |
| Disintegration Time (seconds) | 25-39 | 45-50 | 45-50 | 35-50 | 10 | 15 | 20-30 | 45-50 |
| Assay (%) | 90.0-110.0 | | | | | | | |

What is claimed:

1. A sublingual tablet in the form of a solid tablet for sublingual administration consisting of:
   19-21 weight percent remdesivir as a free base, a pharmaceutically acceptable salt, or a solvate thereof;
   58-61 weight percent mannitol;
   0.5-1.5 weight percent povidone;
   7-9 weight percent crospovidone;
   1-3 weight percent poloxamer;
   4-6 weight percent citric acid as a pH regulating agent;
   2-4 weight percent colloidal silicon dioxide;
   1.5-3 weight percent magnesium stearate; and
   a sweetener,
   wherein the remdesivir free base, pharmaceutically acceptable salt, or solvate thereof is present in an amount from about 0.1 mg to about 50 mg, wherein the composition releases at least 80% of the remdesivir in 15 minutes or less when measured in 900 ml of 0.1N Hydrochloric acid using a USP II apparatus (Paddle) at a temperature of 37+0.5° C. and a rotation speed of 50 revolutions per minute.

2. The sublingual tablet of claim 1, wherein the pH is measured to be between 3.5 and 4.0.

3. A sublingual tablet consisting of:
   about 13-14 weight percent remdesivir as a free base, a pharmaceutically acceptable salt, or a solvate thereof;
   25-27 weight percent microcrystalline cellulose;
   1-2 weight percent cyclodextrin;
   0.5-1.5 weight percent povidone;
   7-9 weight percent crospovidone;
   2-4 weight percent silicon dioxide;
   1.5-3 weight percent magnesium stearate;
   a sweetener;
   an optional flavor; and
   1 N hydrochloric acid as a solvent or pH regulating agent,
   wherein the remdesivir free base, pharmaceutically acceptable salt, or solvate thereof is present in an amount from about 0.1 mg to about 50 mg, wherein the composition releases at least 80% of the remdesivir in 15 minutes or less when measured in 900 ml of 0.1N Hydrochloric acid using a USP II apparatus (Paddle) at a temperature of 37+0.5° C. and a rotation speed of 50 revolutions per minute.

4. The pharmaceutical composition according to claim 1, wherein the composition is prepared by wet granulation process.

5. The pharmaceutical composition according to claim 4, wherein the solvent used in the preparation of the composition is selected from the group consisting of aqueous, alcoholic, hydro-alcoholic, ether, acidic solvent and mixtures thereof.

6. The pharmaceutical composition according to claim 5, wherein the solvent used in the preparation of the composition is selected from the group consisting of ethanol, water, tetrahydrofuran, hydrochloric acid and mixtures thereof.

7. A method for treating, preventing, ameliorating, and/or delaying the onset of one or more symptoms associated with or resulting from a viral infection in a subject caused by members of the filoviridae, flaviviridae paramyxoviridae, orthomyxoviridae, coronaviridae, arenaviridae or adenoviridae families, the method comprising sublingual administration of the pharmaceutical composition according to claim 1.

8. The method according to claim 7, wherein the viral infection is a coronavirus infection.

9. The pharmaceutical composition according to claim 3, wherein the composition is prepared by wet granulation process.

10. The pharmaceutical composition according to claim 9, wherein the solvent used in the preparation of the composition is selected from the group consisting of aqueous, alcoholic, hydro-alcoholic, ether, acidic solvent and mixtures thereof.

11. The pharmaceutical composition according to claim 10, wherein the solvent used in the preparation of the composition is selected from the group consisting of ethanol, water, tetrahydrofuran, hydrochloric acid and mixtures thereof.

12. A method for treating, preventing, ameliorating, and/or delaying the onset of one or more symptoms associated with or resulting from a viral infection in a subject caused by members of the filoviridae, flaviviridae paramyxoviridae, orthomyxoviridae, coronaviridae, arenaviridae or adenoviridae families, the method comprising sublingual administration of the pharmaceutical composition according to claim 3.

13. The method according to claim 12, wherein the viral infection is a coronavirus infection.

14. A sublingual tablet in the form of a solid tablet consisting of:
- 19-21 weight percent remdesivir as a free base, a pharmaceutically acceptable salt, or a solvate thereof;
- 58-61 weight percent mannitol;
- 0.5-1.5 weight percent povidone;
- 7-9 weight percent crospovidone;
- 1-3 weight percent poloxamer;
- 4-6 weight percent citric acid;
- 2-4 weight percent colloidal silicon dioxide;
- 1.5-3 weight percent magnesium stearate; and
- a sweetener.

15. The pharmaceutical composition according to claim 14, wherein the composition is prepared by wet granulation process.

16. The pharmaceutical composition according to claim 15, wherein the solvent used in the preparation of the composition is selected from the group consisting of aqueous, alcoholic, hydro-alcoholic, ether, acidic solvent and mixtures thereof.

17. The pharmaceutical composition according to claim 16, wherein the solvent used in the preparation of the composition is selected from the group consisting of ethanol, water, tetrahydrofuran, hydrochloric acid and mixtures thereof.

18. A method for treating, preventing, ameliorating, and/or delaying the onset of one or more symptoms associated with or resulting from a viral infection in a subject caused by members of the filoviridae, flaviviridae paramyxoviridae, orthomyxoviridae, coronaviridae, arenaviridae or adenoviridae families, the method comprising sublingual administration of the pharmaceutical composition according to claim 14.

19. The method according to claim 18, wherein the viral infection is a coronavirus infection.

20. The pharmaceutical composition according to claim 14, wherein the composition releases at least 80% of the remdesivir in 15 minutes or less when measured in 900 ml of 0.1N Hydrochloric acid using a USP II apparatus (Paddle) at a temperature of $37+0.5°$ C. and a rotation speed of 50 revolutions per minute.

* * * * *